US012320933B2

(12) United States Patent
Li et al.

(10) Patent No.: US 12,320,933 B2
(45) Date of Patent: Jun. 3, 2025

(54) METHOD FOR CORRECTION OF CORRELATED COUNT LOSSES

(71) Applicant: CANON MEDICAL SYSTEMS CORPORATION, Tochigi (JP)

(72) Inventors: Xiaoli Li, Vernon Hills, IL (US); Yi Qiang, Vernon Hills, IL (US); Jeffrey Kolthammer, Vernon Hills, IL (US); Masaki Miyahara, Otawara Tochigi (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 296 days.

(21) Appl. No.: 17/960,689

(22) Filed: Oct. 5, 2022

(65) Prior Publication Data
US 2024/0125951 A1    Apr. 18, 2024

(51) Int. Cl.
*G01T 1/29*     (2006.01)
*A61B 6/03*     (2006.01)
*A61B 6/42*     (2024.01)
*G06T 11/00*    (2006.01)

(52) U.S. Cl.
CPC ............ *G01T 1/2985* (2013.01); *A61B 6/037* (2013.01); *A61B 6/4241* (2013.01); *G06T 11/003* (2013.01)

(58) Field of Classification Search
CPC ..... A61B 6/067; A61B 6/4241; A61B 6/5205; G01T 1/2985; G01T 1/1647
See application file for complete search history.

(56) References Cited

U.S. PATENT DOCUMENTS

| 2006/0091314 | A1 | 5/2006 | Williams et al. |
| 2017/0371046 | A1 | 12/2017 | Laurence et al. |
| 2018/0114345 | A1* | 4/2018 | Liu ........................ G06T 11/005 |
| 2019/0365341 | A1 | 12/2019 | Chan et al. |

(Continued)

FOREIGN PATENT DOCUMENTS

| CN | 107976706 B | | 10/2019 | |
| CN | 106725573 B | * | 12/2019 | ............. A61B 6/037 |
| JP | 2024014781 A | * | 2/2024 | ........... A61B 6/4241 |

OTHER PUBLICATIONS

Extended European Search Report issued Feb. 26, 2024 in European Patent Application 23201886.1, 10 pages.

(Continued)

*Primary Examiner* — Dani Fox
*Assistant Examiner* — Casey Bryant
(74) *Attorney, Agent, or Firm* — Oblon, McClelland, Maier & Neustadt, L.L.P.

(57) ABSTRACT

A positron emission tomography (PET) scanner is provided having a plurality of detector subsystems, including processing circuitry to determine, for each detector subsystem of the plurality of detector subsystems, a singles count loss correction factor of the detector subsystem; determine, for each detector subsystem pair of a plurality of pairs of the detector subsystems, a coincidence count loss correction factor for the detector subsystem pair; calculate a scanner coincidence count loss correction factor for the PET scanner based on the coincidence count loss correction factors determined for the plurality of pairs of the detector subsystems; and reconstruct an image based on the calculated scanner count loss correction factor and scan data acquired from a scan of a patient performed using the PET scanner.

17 Claims, 5 Drawing Sheets

(56) References Cited

U.S. PATENT DOCUMENTS

| | | |
|---|---|---|
| 2022/0104787 A1 | 4/2022 | Chan et al. |
| 2022/0110600 A1 | 4/2022 | Chan et al. |
| 2024/0008832 A1 | 1/2024 | Chan et al. |
| 2024/0023911 A1 * | 1/2024 | Qiang .................. A61B 6/583 |

OTHER PUBLICATIONS

Karp, et al., "Singles Transmission in Positron Emission Tomography Using 137CS", 1995 IEEE, Nuclear Science Symposium and Medical Imaging Conference Record, vol. 3, Oct. 21, 1995, XP000632540, pp. 1363-1367.

Oliver, et al., "Improving the singles rate method for modeling accidental coincidences in high-resolution PET" Physics in Medicine and Biology, vol. 55, No. 22, Nov. 3, 2010, XP020199501, pp. 6951-6971.

* cited by examiner

METHOD FOR CORRECTION OF CORRELATED COUNT LOSSES

BACKGROUND

Field

The present disclosure relates a method for count loss correction due in a radiation diagnosis apparatus such as a Positron Emission Tomography (PET) scanning apparatus.

Description of the Related Art

In a PET scanning apparatus, voxel values in reconstructed images can be calibrated in absolute units of radioactivity concentration with reasonable accuracy and precision. PET scanners include a plurality of subsystems and/or detector units, each requiring a minimum amount of time to process an event and/or read, write, and transfer a certain amount of data. In order to generate quantitative PET images across a wide range of phantoms and source activities, count loss arising from various sources, which can be count-rate dependent and vary by subsystem, needs to be characterized and corrected.

In conventional approaches, count loss correction can be performed by constructing a look-up table of count loss correction (CLC) factors for the entire PET scanner system, which can be derived from decaying source measurements or from simulation. However, this simplistic approach does not account for spatial variations in source distribution that can change the relative count loss in different subsystems or detector units within the scanner.

Count loss correction can also be performed by modelling the count loss behaviour of each subsystem or each detector unit, and then combining them together to model the count loss behaviour of the entire PET scanner system. However, due to the complex nature of count loss in a PET scanner, methods of combining the count loss behaviour of each subsystem or each detector unit face many challenges.

In particular, PET image reconstruction requires coincidence detection, and a coincidence count loss correction factor is usually calculated as the product of the two singles count loss correction factors. However, this approach is not accurate when the count loss for the two singles events in the coincidence event is correlated, meaning that when one singles event is lost, the other singles event has a bigger chance of being lost.

Further, in a PET scanner, different detector units could receive different count rates, and thus experience different count loss. Thus, calculating a system count loss correction factor based on the overall system count rate is not accurate.

In addition, for a PET scan with a long scan duration comparing with the isotope half-life, such as several minutes for a $^{82}$Rb scan, the count rate changes significantly during the scan, and thus the count loss changes significantly during the scan. Accordingly, calculating an overall count loss correction factor based on an average count rate is not accurate.

As discussed above, during reconstruction, a correction factor is applied to the measured count rate to estimate the actual detected count rate, e.g., using:

$$f_{detected} = f_{measured} \cdot C_{single}(f_{measured}), \quad (1)$$

where $C_{single}(f_{measured})$ is the singles count loss correction (CLC) factor and is usually greater than one. An explicit analytical form of $C_{single}(f_{measured})$ generally does not exist. Therefore, in practice, either an approximated analytical form or a lookup table is used instead.

In PET reconstruction, since pairs of photon events are used, the pairs count loss correction (CLC) factor needs to be calculated. For most systems, the pairs CLC factor for an event with singles a and b is given by $$C_{pair}(a,b) = C_{single}(f_a) \cdot C_{single}(f_b), \quad (2)$$

where $f_a$ and $f_b$ are the count rates of each detector. The pairs CLC factor can be either estimated and applied on an event-by-event basis in the reconstruction process, or an average pairs CLC factor can be calculated and applied as a scaling factor to the reconstructed image.

The overall pairs CLC factor can be further simplified as a function of the system singles rate as:

$$C_{pair} = C_{pair}(f_{total\ singles}) = C_{single}^2(f_{total\ singles}). \quad (3)$$

SUMMARY

An embodiment of the present disclosure is directed to a positron emission tomography (PET) scanner having a plurality of detector subsystems, comprising processing circuitry configured to determine, for each detector subsystem of the plurality of detector subsystems, a singles count loss correction factor of the detector subsystem; determine, for each detector subsystem pair of a plurality of pairs of the detector subsystems, a coincidence count loss correction factor for the detector subsystem pair; calculate a scanner coincidence count loss correction factor for the PET scanner based on the coincidence count loss correction factors determined for the plurality of pairs of the detector subsystems; and reconstruct an image based on the calculated scanner count loss correction factor and scan data acquired from a scan of a patient performed using the PET scanner.

Another embodiment of present disclosure is directed to a method of count loss correction for a positron emission tomography (PET) scanner having a plurality of detector subsystems, the method comprising determining, for each detector subsystem of the plurality of detector subsystems, a singles count loss correction factor of the detector subsystem; determining, for each detector subsystem pair of a plurality of pairs of the detector subsystems, a coincidence count loss correction factor for the detector subsystem pair; calculating a scanner coincidence count loss correction factor for the PET scanner based on the coincidence count loss correction factors determined for the plurality of pairs of the detector subsystems; and reconstructing an image based on the calculated scanner count loss correction factor and scan data acquired from a scan of a patient performed using the PET scanner.

A further embodiment of present disclosure is directed to a non-transitory computer-readable medium storing a program that when executed by processing circuitry of a positron emission tomography (PET) scanner having a plurality of detector subsystems, causes the processing circuitry to perform a method of count loss correction for, the method comprising: determining, for each detector subsystem of the plurality of detector subsystems, a singles count loss correction factor of the detector subsystem; determining, for each detector subsystem pair of a plurality of pairs of the detector subsystems, a coincidence count loss correction factor for the detector subsystem pair; calculating a scanner coincidence count loss correction factor for the PET scanner based on the coincidence count loss correction factors determined for the plurality of pairs of the detector subsystems; and reconstructing an image based on the calculated scanner count loss correction factor and scan data acquired from a scan of a patient performed using the PET scanner.

BRIEF DESCRIPTION OF THE DRAWINGS

The application will be better understood in light of the description which is given in a non-limiting manner, accompanied by the attached drawings in which.

DETAILED DESCRIPTION

In one embodiment, when the count loss for two singles events in one coincidence event are correlated, the coincidence count loss correction factor is calculated as the maximum of the two singles count loss correction factor.

Further, in one embodiment, when different detector units experience different count loss, the relative count loss correction factors between different detector units is incorporated into image reconstruction to provide more uniform images, and the system count loss correction factor is calculated as the detector-unit-pair count loss correction factors weighted by the corresponding detector-unit-pair coincidence count rate.

Further, in one embodiment, when the count rate changes significantly during the scan, the overall count loss correction factor for the entire scanner is calculated as the instantaneous count loss correction factors weighted by the corresponding instantaneous coincidence count rate.

Figure 1:
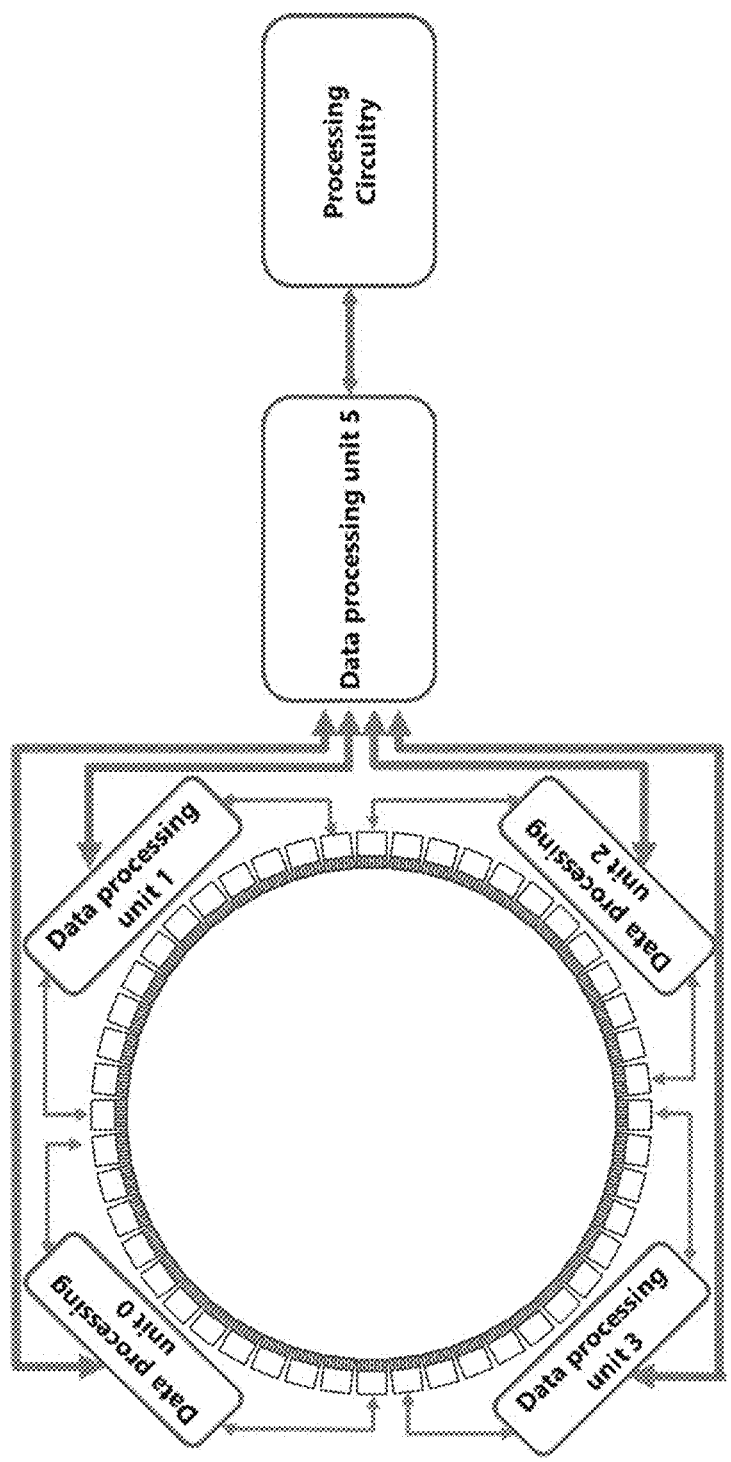
FIG. 1 illustrates detector units and various data processing units in an example PET scanner system.

As shown in FIG. 1, in an example PET scanner system, each of four quadrant data processing units (e.g., data processing unit 0 through data processing unit 3) collect and process data from a number of associated detector units. Further, data processing unit 5 collects and processes data from each of the data processing units 0-3, and further processing and control is performed by processing circuitry connected to data processing unit 5. The data transfer between detector units, data processing units, and the processing circuitry is performed through fiber-optic cable or Ethernet, for example.

Singles Count Loss Correction Factor

Singles count loss correction factors for each subsystem or each detector unit can be calculated from decaying source measurements or via simulation, and/or based on the signal-processing-speed limitations of each subsystem.

For example, each detector unit can experience a random dead time. The singles count loss correction factor for each detector unit can be calculated from a decaying phantom placed at the center of the detector ring. In particular, when placing a decaying phantom at the center, each detector unit receives a similar singles rate, and thus experiences a similar singles count loss. Further, the coincidence count loss correction factor can be calculated from the system singles rate or an average detector unit singles rate. Further, based on equation (3) above, the singles count loss correction factor for each detector unit can be calculated as the square root of the coincidence count loss correction factor. The system pairs rate can also be calculated as: (prompt rate−random rate)×(1−scatter fraction) for a slightly more accurate result, if the scatter fraction as a function of time is available.

Further, if a detector subsystem has an event signal-processing-speed limitation, the singles count loss correction factor for the subsystem can be calculated as an input count rate divided by an event signal-processing-speed threshold. In one embodiment, the relative count loss correction factors between different detector units are incorporated into image reconstruction to provide more uniform images.

Coincidence Count Loss Correction Factor

Coincidence count loss correction factors for each pair of subsystems or detector units can be calculated from the singles count loss correction factors for each subsystem or each detector unit in the pair.

For uncorrelated count loss, e.g. for random dead time, the count loss of the two singles events are independent of each other. The coincidence count loss correction factor is the product of the two singles count loss factors in the coincidence pair.

For correlated count loss, e.g. an overflow due to a limited buffer depth, when the singles event incident on a subsystem with a higher singles rate is lost, the other singles event is also lost. Accordingly, the coincidence count loss correction factor is the maximum of the two singles count loss correction factors in the pair.

For combined uncorrelated and correlated count loss, the uncorrelated and correlated count losses need to be determined separately in order to properly calculate the combined coincidence count loss correction factor. For example, if the root cause of the count loss is known, a simple model can be used to separate the uncorrelated and correlated count loss. If the root cause of the count loss is unknown, a more advanced method is used to separate the uncorrelated and correlated count loss. For example, as discussed in more detail below, a neural network can be trained with different phantom scans to separate the uncorrelated and correlated count losses for a particular scan.

If the root cause of the count loss is known, in one embodiment, the coincidence count loss correction factor for combined uncorrelated and correlated count losses is calculated as follows. First, pre-calibrate the singles count loss correction factor per subsystem due to uncorrelated count loss using a decaying phantom at the center, and save the results as a singles count loss correction table. Note that the uncorrelated count loss, such as due to a random dead time, usually happens at lower count rates than the correlated count loss. Thus, the activity can be controlled so that only correlated count loss occurs.

Next, the singles count loss correction factor per subsystem due to correlated count loss can be calculated using an event processing speed threshold. Suppose a PET scanner has N detector subsystems, and each subsystem i has an event processing speed limit value of $T_i$ (in units of count rate) and the measured input singles rate for the subsystem i is $SR_i$. Further, suppose that the coincident rate per subsystem pair i-j is $CR_{ij}$. The uncorrelated singles count loss (SCL) correction factor for subsystem i, $SCL_{uncor\_j}$ can be calculated based on the input singles rate $SR_i$ and the pre-calibrated single count loss correction table. Further, the correlated SCL correction factor for subsystem i can be calculated as $SC_{corr\_j} = SR_i/T_i$.

Further, in this embodiment, the overall singles count loss correction factor subsystem i can be calculated as $SCL_i = SCL_{uncorr\_i} \times SCL_{corr\_i}$. Further, the coincidence count loss (CCL) correction factor for subsystem pair i-j per acquisition can be calculated as $$CCL_{ij} = SCL_{uncorr\_i} \times SCL_{uncorr\_j} \times \max(SCL_{corr\_i}, SCL_{corr\_j}).$$

Next, the relative singles count loss correction factor per subsystem i can be calculated as $SCL_{rel\_i} = SCL_i/\text{mean}(SCL_i)$ and can be multiplied by values from the crystal efficiency table during image reconstruction to achieve more uniform images. The coincidence count loss correction factor for scanner can be calculated as:

$$\frac{\sum_{ij}(CCL_{ij} \times CR_{ij})}{\sum_{ij} CR_{ij}}$$

Note that the coincidence count loss correction factor for the scanner can be used as a scaling factor applied to the reconstructed images to achieve better image quantitation metrics, such as the standard update value (SUV).

If the root cause of the count loss is unknown, in one embodiment, the coincidence count loss correction factor for the combined uncorrelated and correlated count losses can be calculated as follows. First, several phantom scans are performed. For example, the phantoms should be of different sizes, which provides a differing amount of scatter events. Further, the phantoms should have both centered and off-centered activity, which provides both symmetric and non-symmetric count rates among the different subsystems. Each phantom scan should be a series of acquisitions which covers a range of activities. In addition, the lowest activity should correspond to almost no count loss. For each phantom scan, the following count rates and activity should be recorded for each acquisition:

Activity per acquisition k: $\text{Activity}_k$
For acquisition k, the input singles rate for subsystem i: $SR_{input\_i\_k}$
For acquisition k, the output singles rate for subsystem i: $SR_{output\_i\_k}$
For acquisition k, the coincidence rate for subsystem pair i-j: $CR_{ij\_k}$ For each phantom scan, the count loss correction factors for each acquisition can be calculated from recorded count rates and activity. In particular, in one embodiment, it is assumed that there is no count loss at the lowest activity ($\text{Activity}_0$). The expected singles rate without count loss for subsystem i for acquisition k can be calculated using the recorded activity and count rate as $SRoutput\_i\_k\_expected\_ = SR_{input\_1\_0} \times \text{Activity}_k/\text{Activity}_0$. Further, the singles count loss correction factor for subsystem for acquisition k can be calculated as $SCL_{i\_k} = SR_{output\_i\_k\_expected}/SR_{i\_k}$.

The expected coincidence rate without count loss per subsystem pair per acquisition could be calculated as $CR_{ij\_k\_expected} = CR_{ij\_0} \times \text{Activity}_k/\text{Activity}_0$. The coincidence count loss correction factor per subsystem pair per acquisition could be calculated as $CCL_{ij\_k} = CR_{ij\_k\_expected}/CR_{ij\_k}$.

For each phantom scan, the count loss correction factors for each acquisition can also be represented using uncorrelated and correlated singles count loss correction factors. For example, suppose the uncorrelated singles count loss factor correction for subsystem i for acquisition k is $SCL_{uncorr\_j\_k}$ and the correlated singles count loss correction factor for subsystem i for acquisition k is $SCL_{corr\_j\_k}$. Then, the singles count loss correction factor for subsystem i for acquisition k can be calculated as $SCL_{i\_k} = SCL_{uncorr\_i\_k} \times SCL_{corr\_i\_k}$. Further, the coincidence count loss correction factor for subsystem pair i-j for acquisition k can be calculated as $CCL_{ij\_k} = SCL_{uncorr\_i\_k} \times SCL_{uncorr\_j\_k} \times \max(SCL_{corr\_i\_k}, SCL_{corr\_j\_k})$.

Further, in one embodiment, a neural network is trained using different phantom scans to estimate the uncorrelated and correlated count losses for a particular scan. In one example implementation, the input layer includes inputs for (1) the singles count loss correction factor for subsystem i for acquisition k ($SCL_{i\_k}$) estimated from recorded count rates and activity for all phantom scans, and/or (2) the coincidence count loss correction factor for subsystem pair i-j per acquisition k ($CCL_{ij\_k}$), which is estimated from recorded count rates and activity for all phantom scans. In this embodiment, the output layer of the neural network includes outputs of (1) the uncorrelated singles count loss correction factor for subsystem i for acquisition k ($SCL_{uncorr\_j\_k}$), and (2) the correlated singles count loss correction factor for subsystem i for acquisition k ($SCL_{corr\_j\_k}$). Next, curve fitting or interpolation can be used to calculate $SCL_{uncorr\_i}$ and $SCL_{corr\_j}$ at different input single rates from plots of $SCL_{uncorr\_i\_k}$ vs $SR_{input\_i\_k}$ and $SCL_{corr\_i\_k}$ vs $SR_{input\_i\_k}$ for each detector subsystem i.

Thus, in one embodiment, for a new patient or phantom scan, for each subsystem i of the scanner, the uncorrelated and correlated singles count loss correction factors ($SCL_{uncor\_j}$ and $SCL_{corr\_j}$) can be calculated based upon the input singles rates, as discussed above using the curve-fitting. Moreover, the singles count loss correction factors for each subsystem i ($SCL_i = SCL_{uncorr\_i} \times SCL_{corr\_i}$) and the coincidence count loss correction factor for each subsystem pair i-j ($CCL_{ij} = SCL_{uncorr\_i} \times SCL_{uncorr\_j} \times \max(SCL_{corr\_i}, SCL_{corr\_j})$) can be calculated as discussed above. Finally, the relative singles count loss correction factor for each subsystem i ($SCL_{rel\_i} = SCL_i/\text{mean}(SCL_i)$) and the coincidence count loss correction factor for the scanner can be calculated as discussed above. As noted above, the relative singles count loss correction factors can be multiplied by values from the crystal efficiency table during image reconstruction to achieve more uniform images, while the coincidence count loss correction factor for the scanner can be used as a scaling factor applied to the reconstructed images to achieve better image quantitation metrics, such as the standard update value (SUV).

In one embodiment, coincidence count loss correction factors for the overall scanner system are calculated from the coincidence count loss correction factors for each pair of subsystems or detector units, using the pairs rate for each pair of subsystems or detector units as weighting factors. In this embodiment, the pairs rate for each pair of subsystems or detector units is calculated as the prompt rate minus the random rate, for example.

In one embodiment, the coincidence count loss correction factors for a whole data frame are calculated from the instantaneous coincidence count loss correction factors, using the instantaneous pairs rate as weighting factors. In one embodiment, the time duration to calculate the instantaneous pairs rate is determined based upon the half-life of the radioisotope. In this embodiment, the pairs rate is calculated as the prompt rate minus the random rate, for example.

Figure 2:
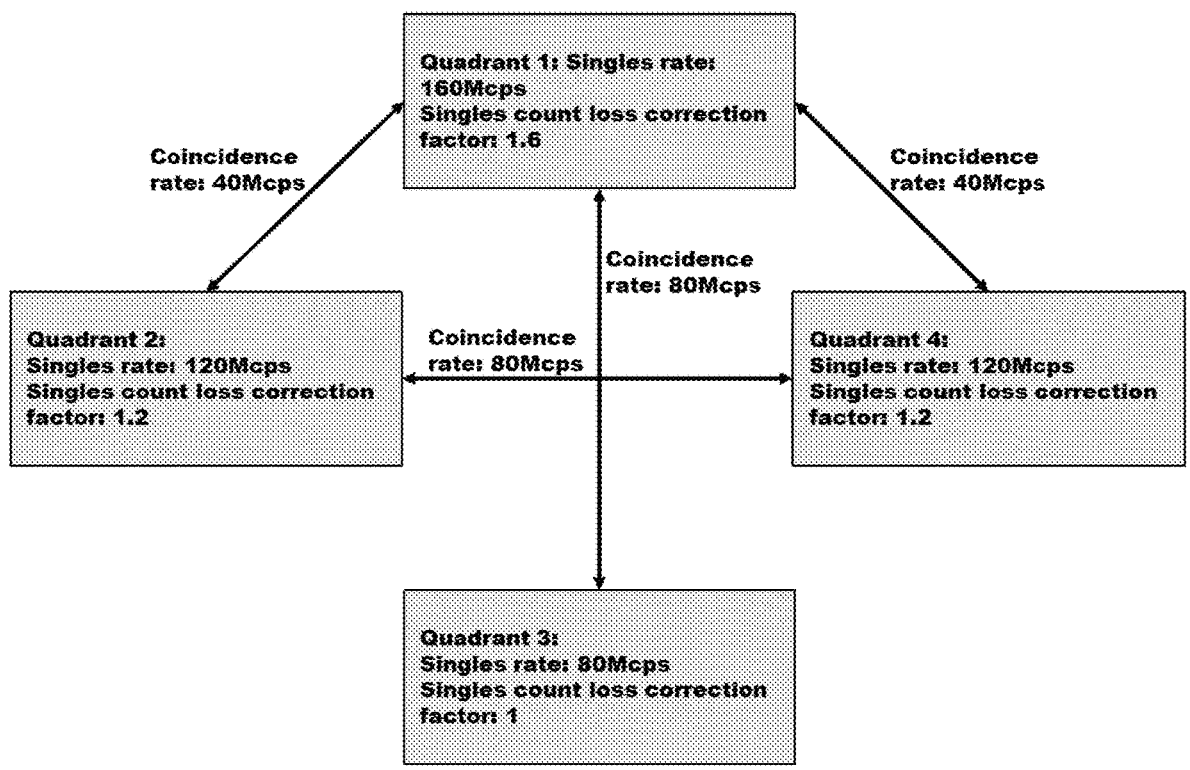
FIG. 2 illustrates an example calculation of the coincidence count loss correction factor for the scanner system shown in FIG. 1.

FIG. 2 illustrates an example calculation of the coincidence count loss correction factor for the overall scanner system shown in FIG. 1, according to one embodiment of the present disclosure. In this example, the PET scanner is split into four quadrants, with each quadrant having an event processing-speed limit of 100 Mcps. Thus, in this example, correlated count loss would begin to occur when the input singles rate to a pair of quadrants exceeds 100 Mcps.

In this example, the measured input singles rate per quadrant is as follows:
Quadrant 1: 160 Mcps,
Quadrant 2: 120 Mcps,
Quadrant 3: 80 Mcps,
Quadrant 4: 120 Mcps.
Further, the measured coincidence rate per quadrant pairs, for selected quadrant pairs, is as follows:
Quadrants 1-2: 40 Mcps,
Quadrants 1-3: 80 Mcps,
Quadrants 1-4: 40 Mcps,
Quadrants 2-4: 80 Mcps.
In this example, the singles count loss correction factor per quadrant is determined as discussed above. In this example, based at least on the event processing-speed limits, the values are:
Quadrant 1: 1.6,
Quadrant 2: 1.2,
Quadrant 3: 1.0,
Quadrant 4: 1.2.
Further, in this example, the relative count loss correction factor for quadrant i for image reconstruction can be calculated as the singles count loss correction factor for quadrant I divided by the mean singles count loss correction factor over all quadrants. In this example, the values are calculated as:
Quadrant 1: 1.28;
Quadrant 2: 0.96;
Quadrant 3: 0.8;
Quadrant 4: 0.96.
Further, in this example, the coincidence count loss correction factor per quadrant pair for correlated count loss is determined as described above. In this example, the values are determined to be:
Quadrants 1-2: 1.6,
Quadrants 1-3: 1.6,
Quadrants 1-4: 1.6,
Quadrants 2-4: 1.2.
Finally, the coincidence count loss correction for the entire scanner is calculated as a weighted average using the coincidence rate per quadrant pair as weighting factors:

$$\frac{1.6 \times 40 + 1.6 \times 80 + 1.6 \times 40 + 1.2 \times 80}{40 + 80 + 40 + 80} = 1.4667$$

In the general case example, suppose a PET scanner has N detector subsystems, and each subsystem has an event processing speed limit value of T (in units of count rate). Thus, in this second example, correlated count loss will occur when the input singles rate to the subsystems exceeds the value T. In this example, assume that the measured input singles rate per subsystem i is $SR_i$ and the measured coincidence rate per subsystem pair i-j is $CR_{ij}$. Thus, based on the event processing speed limitation value of each subsystem, the singles count loss correction factor for subsystem i is $SCL_{corr\_i}=SR_i/T$.

Further, in this example, the relative count loss correction factor for subsystem i for image reconstruction can be calculated as $SCL_{rel\_corr\_i}=SCL_{corr\_i}/\text{mean}(SCL_{corr\_i})$, where mean($SCL_{corr\_i}$) is the mean singles count loss correction factor over all subsystems.

Further, in this example, the coincidence count loss correction factor per subsystem pair i-j for correlated count loss is calculated as $CCL_{ij}=\max(SCL_{corr\_i}, SCL_{corr\_j})$.

Further, in this example, the coincidence count loss correction factor for the overall scanner is a weighted average given by:

$$\frac{\sum_{ij}(CCL_{ij} \times CR_{ij})}{\sum_{ij} CR_{ij}}$$

Inventions of the present disclosure have several advantages over existing approaches. In particular, the inventions disclosed herein provide a practical and more accurate method for count loss correction, especially when the count loss for the two singles events in one coincidence event pair are correlated.

Figure 3:
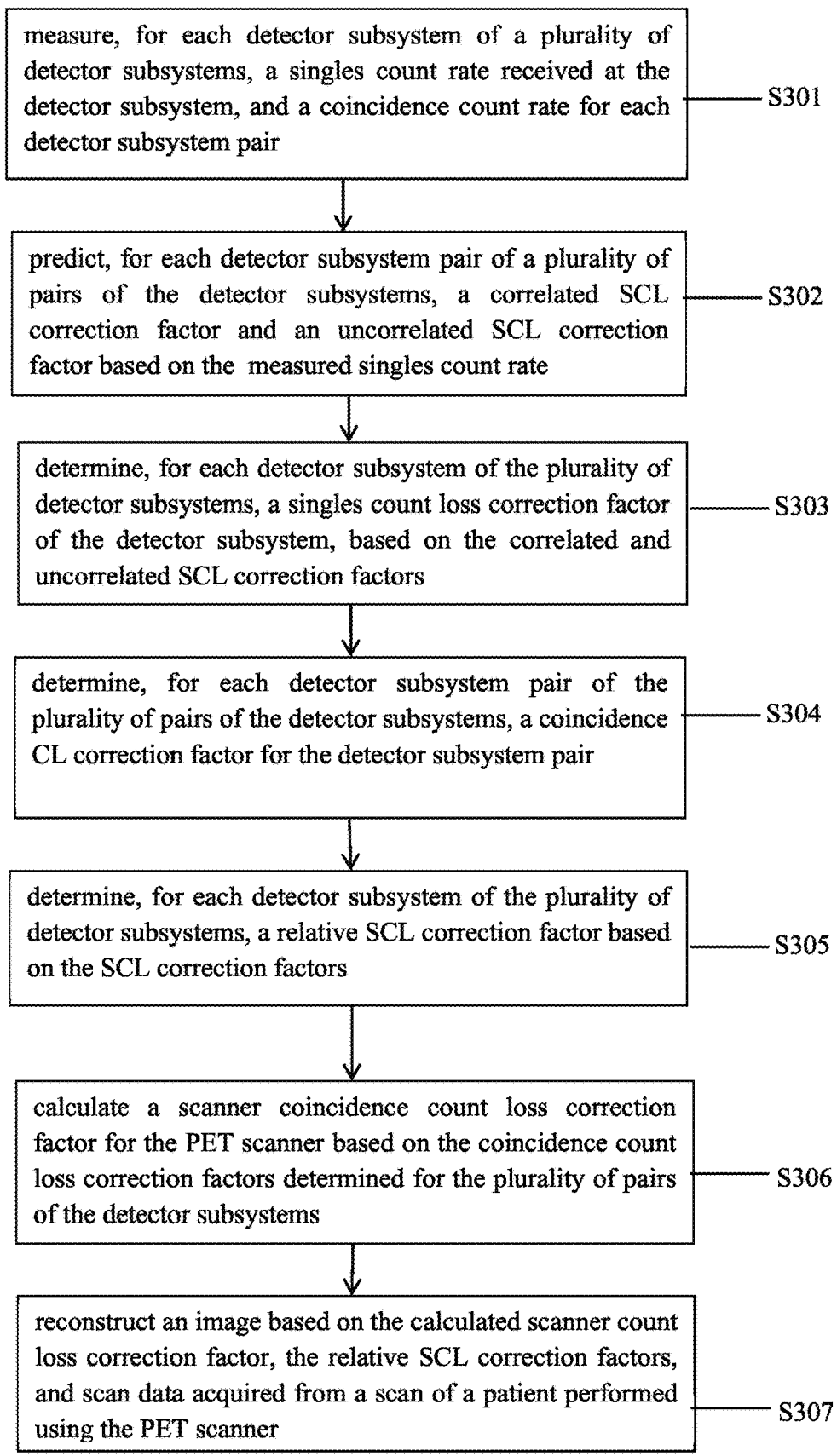
FIG. 3 is a flowchart of a method according to the present disclosure.

FIG. 3 illustrates a flowchart of a method of count loss correction for a positron emission tomography (PET) scanner having a plurality of detector subsystems according to one embodiment of the present disclosure.

In step S301, for each detector subsystem of a plurality of detector subsystems, a singles count rate received at the detector subsystem is measured. Further, for each detector subsystem pair of a plurality of pairs of the detector subsystems, a coincidence count rate for detector subsystem pair is measured.

In step S302, for each detector subsystem pair of a plurality of pairs of the detector subsystems, a correlated SCL correction factor and an uncorrelated SCL correction factor is predicted based on the measured singles count rate using estimated curves generated using the trained neural network, as discussed above.

In step S303, for each detector subsystem of the plurality of detector subsystems, a singles count loss correction factor of the detector subsystem is determined based on the correlated and uncorrelated SCL correction factors, as discussed above.

Then, in step S304, for each detector subsystem pair of the plurality of pairs of the detector subsystems, a coincidence CL correction factor is determined for the detector subsystem pair based on the correlated and uncorrelated SCL correction factors, as discussed above.

In step S305, for each detector subsystem of the plurality of detector subsystems, a relative SCL correction factor is determined based on the SCL correction factors.

In step S306, a scanner coincidence count loss correction factor for the PET scanner is calculated based on the coincidence count loss correction factors determined for the plurality of pairs of the detector subsystems.

In step S307, a PET image is reconstructed based on the calculated scanner count loss correction factor and scan data acquired from a scan of on object performed using the PET scanner. The relative SCL correction factors of each subsystem can also be used in the reconstruction, as discussed above.

Figure 4:
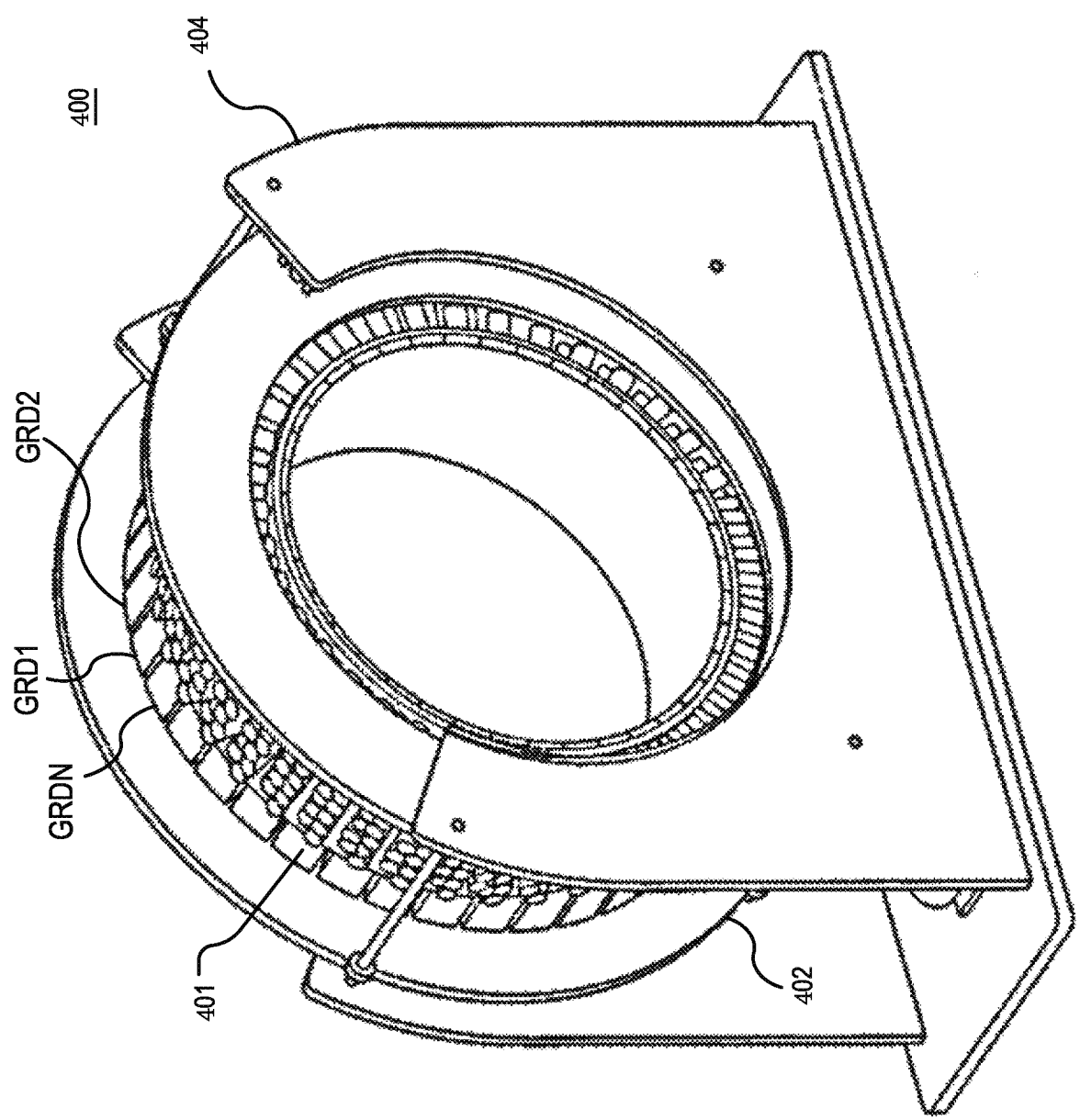
FIG. 4 is an illustration of a perspective view of a positron emission tomography (PET) scanner according to one embodiment of the present disclosure.
Figure 5:
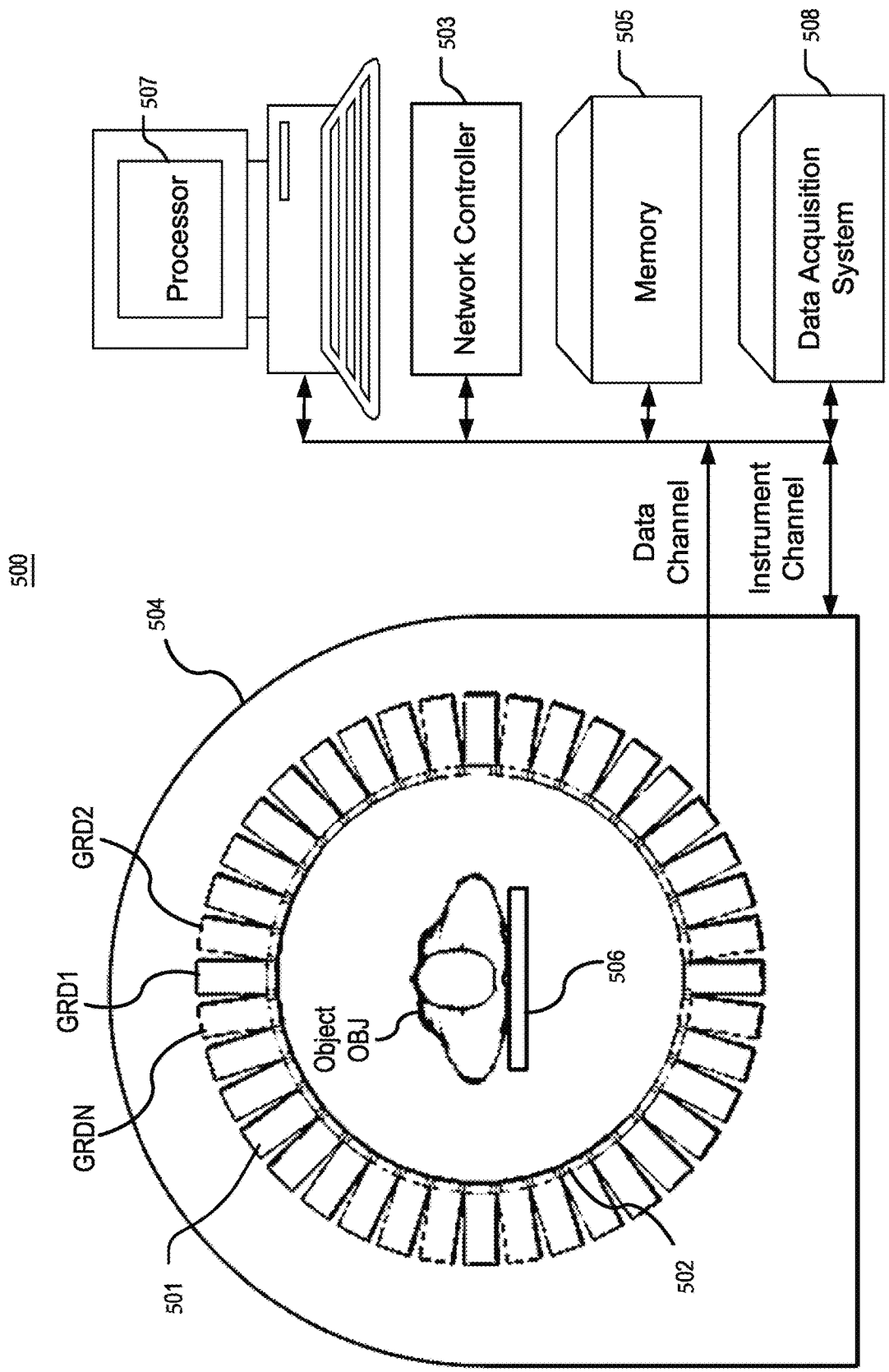
FIG. 5 is a schematic of a PET scanner apparatus and associated hardware, according to one embodiment of the present disclosure.

A PET scanner that can be used in the embodiments disclosed herein is shown in FIGS. 4 and 5. PET scanner 400 includes a plurality of gamma-ray detectors (GRDs) 401 (e.g., GRD1, GRD2, through GRDN) that are each configured as rectangular detector modules. According to one implementation, the detectors are arranged in a ring, which forms a circular bore 402 about a gantry 404. In this example, the ring includes 40 GRDs 401. A ring may have a different number of GRDs 401 depending on factors such as the desired size of bore 402. The GRDs 401 include scintillator crystal arrays for converting the gamma rays into scintillation photons (e.g., at optical, infrared, and ultraviolet wavelengths), which are detected by photodetectors. Each GRD 401 can include a two-dimensional array of individual detector crystals, which absorb gamma radiation and emit scintillation photons, or can include a monolithic array or a slatted array. The scintillation photons can be detected by a two-dimensional array of devices such as SiPMs (not shown) that are also arranged in the GRD 401. A light guide can be disposed between the array of detector crystals and the SiPMs. The crystal and SiPM arrangements according to the present disclosure are discussed in more detail below.

FIG. 4 shows a schematic view of a PET scanner system having GRDs arranged to detect gamma-rays emitted from an object OBJ. The GRDs can measure the timing, position, and energy corresponding to each detected gamma-ray. It can be appreciated that the single PET detector ring of FIG. 4 can be extrapolated to include any number of PET detector rings along an axial length of the PET scanner.

FIG. 5 shows an example of the arrangement of a PET scanner 500, in which the object OBJ to be imaged rests on a table 506 and the GRD modules GRD1 through GRDN are arranged circumferentially around the object OBJ and the table 506. The GRDs can comprise a PET detector ring and may be fixedly-connected to a circular bore 502 that is fixedly-connected to a gantry 504. The gantry 504 houses many parts of the PET scanner. The gantry 504 of the PET scanner also includes an open aperture, defined by the cylindrical bore 502, through which the object OBJ and the table 506 can pass, and gamma-rays emitted in opposite directions from the object OBJ due to an annihilation event can be detected by the GRDs and timing and energy information can be used to determine coincidences for gamma-ray pairs.

In FIG. 5, circuitry and hardware are also shown for acquiring, storing, processing, and distributing gamma-ray detection data. The circuitry and hardware include a processor (processing circuitry) 507, a network controller 503, a memory 505, and a data acquisition system (DAS) 508. The PET imager also includes a data channel that routes detection measurement results from the GRDs to the DAS 508, the processor 507, the memory 505, and the network controller 503. The data acquisition system 508 can control the acquisition, digitization, and routing of the detection data from the detectors. In one implementation, the DAS 508 controls the movement of the table 506. The processor 507 performs functions including identifying arrangement errors, pre-reconstruction processing of the detection data, image reconstruction, and post-reconstruction processing of the image data.

According to an embodiment, the processor 507 of the PET scanner 500 of FIG. 5 can be configured to perform the methods as described herein. The processor 507 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 505 can be a hard disk drive, CD-ROM drive, DVD drive, FLASH drive, RAM, ROM or any other electronic storage known in the art. The memory 505 may be non-volatile, such as ROM, EPROM, EEPROM or FLASH memory. The memory 505 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 507 can execute a computer program including a set of computer-readable instructions that perform methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel or an Opteron processor from AMD and an operating system, such as Microsoft VISTA, UNIX, Solaris, LINUX, Apple, MAC-OS and other operating systems known to those skilled in the art. Further, the CPU can be implemented as multiple processors cooperatively working in parallel to perform the instructions. The instructions may be stored in memory 505 or within a memory located in network controller 503 (not shown).

In one implementation, the PET scanner may include a display for displaying a reconstructed image and the like. The display can be an LCD display, CRT display, plasma display, OLED, LED or any other display known in the art.

The network controller 503, such as an Intel Ethernet PRO network interface card from Intel, can interface between the various parts of the PET imager. Additionally, the network controller 503 can also interface with an external network. As can be appreciated, the external network can be a public network, such as the Internet, or a private network such as an LAN or WAN network, or any combination thereof and can also include PSTN or ISDN subnetworks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Additional embodiments are provided by way of example in the following parentheticals.

(1) A positron emission tomography (PET) scanner having a plurality of detector subsystems, comprising:
processing circuitry configured to
determine, for each detector subsystem of the plurality of detector subsystems, a singles count loss correction factor of the detector subsystem;
determine, for each detector subsystem pair of a plurality of pairs of the detector subsystems, a coincidence count loss correction factor for the detector subsystem pair;
calculate a scanner coincidence count loss correction factor for the PET scanner based on the coincidence count loss correction factors determined for the plurality of pairs of the detector subsystems; and
reconstruct an image based on the calculated scanner coincidence count loss correction factor and scan data acquired from a scan of a patient performed using the PET scanner.

(2) The PET scanner of (1), wherein the processing circuitry is further configured to determine, for each detector subsystem of the plurality of detector subsystems, the singles count loss correction factor of the detector subsystem based on a processing-speed threshold of the detector subsystem.

(3) The PET scanner of (2), wherein the processing circuitry is further configured to determine, for each detector subsystem of the plurality of detector subsystems, the singles count loss correction factor of the detector subsystem based on a measured singles count rate received at the detector subsystem.

(4) The PET scanner of (1), wherein the processing circuitry is further configured to calculate the scanner coincidence count loss correction factor for the PET scanner based on a measured coincidence count rate for each detector subsystem pair of the plurality of pairs of the detector subsystems.

(5) The PET scanner (4), wherein the processing circuitry is further configured to calculate the scanner coincidence count loss correction factor for the PET scanner as a weighted combination of the coincidence count loss correction factors determined for the plurality of pairs of the detector subsystems using a corresponding set of weights, the set of weights being the measured coincidence count rates for the plurality of pairs of the detector subsystems.

(6) The PET scanner (1), wherein the processing circuitry is further configured to
  determine that count loss for a particular detector subsystem pair, of the plurality of pairs of the detector subsystems, is correlated; and
  determine the coincidence count loss correction factor for the particular detector subsystem pair by taking a maximum of the singles count loss correction factors of the detector subsystems included in the particular detector subsystem pair.

(7) The PET scanner of (1), wherein the processing circuitry is further configured to
  predict, for each detector subsystem of the plurality of detector subsystems, a correlated singles count loss correction factor and an uncorrelated singles count loss correction factor, based on a measured singles count rate received at the detector subsystem; and
  determine, for each detector subsystem of the plurality of detector subsystems, the singles count loss correction factor of the detector subsystem by multiplying the correlated singles count loss correction factor by the uncorrelated singles count loss correction factor.

(8) The PET scanner of (7), wherein the processing circuitry is further configured to predict, for each detector subsystem of the plurality of detector subsystems, the correlated singles count loss correction factor from a first function relating the measured singles count rate received at the detector subsystem to the correlated singles count loss correction factor at the detector subsystem, and a second function relating the measured singles count rate received at the detector subsystem to the uncorrelated singles count loss correction factor at the detector subsystem, the first and second function being determined from outputs of a trained neural network that was trained to output a particular correlated singles count loss correction factor and a particular uncorrelated singles count loss correction factor for a corresponding particular input singles count rate.

(9) The PET scanner of (1), wherein the processing circuitry is further configured to determine, for each detector subsystem of the plurality of detector subsystems, a relative singles count loss correction factor; and reconstruct the image based on the calculated scanner coincidence count loss correction factor, the determined relative singles count loss correction factors, and the scan data.

(10) A method of count loss correction for a positron emission tomography (PET) scanner having a plurality of detector subsystems, the method comprising:
  determining, for each detector subsystem of the plurality of detector subsystems, a singles count loss correction factor of the detector subsystem;
  determining, for each detector subsystem pair of a plurality of pairs of the detector subsystems, a coincidence count loss correction factor for the detector subsystem pair;
  calculating a scanner coincidence count loss correction factor for the PET scanner based on the coincidence count loss correction factors determined for the plurality of pairs of the detector subsystems; and
  reconstructing an image based on the calculated scanner coincidence count loss correction factor and scan data acquired from a scan of a patient performed using the PET scanner.

(11) The method of (10), further comprising determining, for each detector subsystem of the plurality of detector subsystems, the singles count loss correction factor of the detector subsystem based on a processing-speed threshold of the detector subsystem.

(12) The method of (11), further comprising determining, for each detector subsystem of the plurality of detector subsystems, the singles count loss correction factor of the detector subsystem based on a measured singles count rate received at the detector subsystem.

(13) The method of (10), further comprising calculating the scanner coincidence count loss correction factor for the PET scanner based on a measured coincidence count rate for each detector subsystem pair of the plurality of pairs of the detector subsystems.

(14) The method of (13), further comprising calculating the scanner coincidence count loss correction factor for the PET scanner as a weighted combination of the coincidence count loss correction factors determined for the plurality of pairs of the detector subsystems using a corresponding set of weights, the set of weights being the measured coincidence count rates for the plurality of pairs of the detector subsystems.

(15) The method of (10), further comprising:
  determining that count loss for a particular detector subsystem pair, of the plurality of pairs of the detector subsystems, is correlated; and
  determining the coincidence count loss correction factor for the particular detector subsystem pair by taking a maximum of the singles count loss correction factors of the detector subsystems included in the particular detector subsystem pair.

(16) The method of (10), further comprising:
  predicting, for each detector subsystem of the plurality of detector subsystems, a correlated singles count loss correction factor and an uncorrelated singles count loss correction factor, based on a measured singles count rate received at the detector subsystem; and
  determining, for each detector subsystem of the plurality of detector subsystems, the singles count loss correction factor of the detector subsystem by multiplying the correlated singles count loss correction factor by the uncorrelated singles count loss correction factor.

(17) The method of (16), wherein the predicting step further comprises:
  predicting, for each detector subsystem of the plurality of detector subsystems, the correlated singles count loss correction factor from a first function relating the measured singles count rate received at the detector subsystem to the correlated singles count loss correction factor at the detector subsystem, and a second function relating the measured singles count rate received at the detector subsystem to the uncorrelated singles count loss correction factor at the detector subsystem, the first and second function being determined from outputs of a trained neural network that was trained to output a particular correlated singles count loss correction factor and a particular uncorrelated singles count loss correction factor for a corresponding particular input singles count rate.

(18) The method of (17), further comprising determining, for each detector subsystem of the plurality of detector subsystems, a relative singles count loss correction factor; and reconstructing the image based on the calculated scanner coincidence count loss correction factor, the determined relative singles count loss correction factors, and the scan data.

(19) A non-transitory computer-readable medium storing a program that when executed by processing circuitry of a positron emission tomography (PET) scanner having a plurality of detector subsystems, causes the processing circuitry to perform a method of count loss correction for, the method comprising:
  determining, for each detector subsystem of the plurality of detector subsystems, a singles count loss correction factor of the detector subsystem;
  determining, for each detector subsystem pair of a plurality of pairs of the detector subsystems, a coincidence count loss correction factor for the detector subsystem pair;
  calculating a scanner coincidence count loss correction factor for the PET scanner based on the coincidence count loss correction factors determined for the plurality of pairs of the detector subsystems; and
  reconstructing an image based on the calculated scanner coincidence count loss correction factor and scan data acquired from a scan of a patient performed using the PET scanner.

(20) The computer-readable medium of (19), wherein the method further comprises:
  determining that count loss for a particular detector subsystem pair, of the plurality of pairs of the detector subsystems, is correlated; and
  determining the coincidence count loss correction factor for the particular detector subsystem pair by taking a maximum of the singles count loss correction factors of the detector subsystems included in the particular detector subsystem pair Numerous modifications and variations of the present disclosure are possible in light of the above teachings. It is therefore to be understood that within the scope of the appended claims, the inventions can be practiced otherwise than as specifically described herein.

The invention claimed is:

1. A positron emission tomography (PET) scanner having a plurality of detector subsystems, comprising:
  processing circuitry configured to
    determine, for each detector subsystem of the plurality of detector subsystems, a singles count loss correction factor of the detector subsystem;
    determine, for each detector subsystem pair of a plurality of pairs of the detector subsystems, a coincidence count loss correction factor for the detector subsystem pair;
    calculate a scanner coincidence count loss correction factor for the PET scanner based on the coincidence count loss correction factors determined for the plurality of pairs of the detector subsystems; and
    reconstruct an image based on the calculated scanner coincidence count loss correction factor and scan data acquired from a scan of a patient performed using the PET scanner,
  wherein the processing circuitry is further configured to determine, for each detector subsystem of the plurality of detector subsystems, the singles count loss correction factor of the detector subsystem based on a processing-speed threshold of the detector subsystem.

2. The PET scanner of claim 1, wherein the processing circuitry is further configured to determine, for each detector subsystem of the plurality of detector subsystems, the singles count loss correction factor of the detector subsystem based on a measured singles count rate received at the detector subsystem.

3. The PET scanner of claim 1, wherein the processing circuitry is further configured to calculate the scanner coincidence count loss correction factor for the PET scanner based on a measured coincidence count rate for each detector subsystem pair of the plurality of pairs of the detector subsystems.

4. The PET scanner of claim 3, wherein the processing circuitry is further configured to calculate the scanner coincidence count loss correction factor for the PET scanner as a weighted combination of the coincidence count loss correction factors determined for the plurality of pairs of the detector subsystems using a corresponding set of weights, the set of weights being the measured coincidence count rates for the plurality of pairs of the detector subsystems.

5. The PET scanner of claim 1, wherein the processing circuitry is further configured to
  determine that count loss for a particular detector subsystem pair, of the plurality of pairs of the detector subsystems, is correlated; and
  determine the coincidence count loss correction factor for the particular detector subsystem pair by taking a maximum of the singles count loss correction factors of the detector subsystems included in the particular detector subsystem pair.

6. The PET scanner of claim 1, wherein the processing circuitry is further configured to
  predict, for each detector subsystem of the plurality of detector subsystems, a correlated singles count loss correction factor and an uncorrelated singles count loss correction factor, based on a measured singles count rate received at the detector subsystem; and
  determine, for each detector subsystem of the plurality of detector subsystems, the singles count loss correction factor of the detector subsystem by multiplying the correlated singles count loss correction factor by the uncorrelated singles count loss correction factor.

7. The PET scanner of claim 6, wherein the processing circuitry is further configured to predict, for each detector subsystem of the plurality of detector subsystems, the correlated singles count loss correction factor from a first function relating the measured singles count rate received at the detector subsystem to the correlated singles count loss correction factor at the detector subsystem, and a second function relating the measured singles count rate received at the detector subsystem to the uncorrelated singles count loss correction factor at the detector subsystem, the first and second function being determined from outputs of a trained neural network that was trained to output a particular correlated singles count loss correction factor and a particular uncorrelated singles count loss correction factor for a corresponding particular input singles count rate.

8. The PET scanner of claim 1, wherein the processing circuitry is further configured to:
- determine, for each detector subsystem of the plurality of detector subsystems, a relative singles count loss correction factor; and
- reconstruct the image based on the calculated scanner coincidence count loss correction factor, the determined relative singles count loss correction factors, and the scan data.

9. A method of count loss correction for a positron emission tomography (PET) scanner having a plurality of detector subsystems, the method comprising:
- determining, for each detector subsystem of the plurality of detector subsystems, a singles count loss correction factor of the detector subsystem;
- determining, for each detector subsystem pair of a plurality of pairs of the detector subsystems, a coincidence count loss correction factor for the detector subsystem pair;
- calculating a scanner coincidence count loss correction factor for the PET scanner based on the coincidence count loss correction factors determined for the plurality of pairs of the detector subsystems; and
- reconstructing an image based on the calculated scanner coincidence count loss correction factor and scan data acquired from a scan of a patient performed using the PET scanner,
- wherein the method further comprises determining, for each detector subsystem of the plurality of detector subsystems, the singles count loss correction factor of the detector subsystem based on a processing-speed threshold of the detector subsystem.

10. The method of claim 9, further comprising determining, for each detector subsystem of the plurality of detector subsystems, the singles count loss correction factor of the detector subsystem based on a measured singles count rate received at the detector subsystem.

11. The method of claim 9, further comprising calculating the scanner coincidence count loss correction factor for the PET scanner based on a measured coincidence count rate for each detector subsystem pair of the plurality of pairs of the detector subsystems.

12. The method of claim 11, further comprising calculating the scanner coincidence count loss correction factor for the PET scanner as a weighted combination of the coincidence count loss correction factors determined for the plurality of pairs of the detector subsystems using a corresponding set of weights, the set of weights being the measured coincidence count rates for the plurality of pairs of the detector subsystems.

13. The method of claim 9, further comprising:
- determining that count loss for a particular detector subsystem pair, of the plurality of pairs of the detector subsystems, is correlated; and
- determining the coincidence count loss correction factor for the particular detector subsystem pair by taking a maximum of the singles count loss correction factors of the detector subsystems included in the particular detector subsystem pair.

14. The method of claim 9, further comprising:
- predicting, for each detector subsystem of the plurality of detector subsystems, a correlated singles count loss correction factor and an uncorrelated singles count loss correction factor, based on a measured singles count rate received at the detector subsystem; and
- determining, for each detector subsystem of the plurality of detector subsystems, the singles count loss correction factor of the detector subsystem by multiplying the correlated singles count loss correction factor by the uncorrelated singles count loss correction factor.

15. The method of claim 14, wherein the predicting step further comprises:
- predicting, for each detector subsystem of the plurality of detector subsystems, the correlated singles count loss correction factor from a first function relating the measured singles count rate received at the detector subsystem to the correlated singles count loss correction factor at the detector subsystem, and a second function relating the measured singles count rate received at the detector subsystem to the uncorrelated singles count loss correction factor at the detector subsystem, the first and second function being determined from outputs of a trained neural network that was trained to output a particular correlated singles count loss correction factor and a particular uncorrelated singles count loss correction factor for a corresponding particular input singles count rate.

16. The method of claim 15, further comprising
- determining, for each detector subsystem of the plurality of detector subsystems, a relative singles count loss correction factor; and
- reconstructing the image based on the calculated scanner coincidence count loss correction factor, the determined relative singles count loss correction factors, and the scan data.

17. A non-transitory computer-readable medium storing a program that when executed by processing circuitry of a positron emission tomography (PET) scanner having a plurality of detector subsystems, causes the processing circuitry to perform a method of count loss correction for, the method comprising:
- determining, for each detector subsystem of the plurality of detector subsystems, a singles count loss correction factor of the detector subsystem;
- determining, for each detector subsystem pair of a plurality of pairs of the detector subsystems, a coincidence count loss correction factor for the detector subsystem pair;
- calculating a scanner coincidence count loss correction factor for the PET scanner based on the coincidence count loss correction factors determined for the plurality of pairs of the detector subsystems; and
- reconstructing an image based on the calculated scanner coincidence count loss correction factor and scan data acquired from a scan of a patient performed using the PET scanner, wherein the method further comprises:
  - determining that count loss for a particular detector subsystem pair, of the plurality of pairs of the detector subsystems, is correlated; and
  - determining the coincidence count loss correction factor for the particular detector subsystem pair by taking a maximum of the singles count loss correction factors of the detector subsystems included in the particular detector subsystem pair.

* * * * *